United States Patent
Roques et al.

Patent Number: 5,741,781
Date of Patent: Apr. 21, 1998

[54] MERCAPTOALKANOYLDIPEPTIDE COMPOUNDS

[75] Inventors: Bernard Pierre Roques, Saint-Maurice; Marie-Claude Fournie-Zaluski, Paris, both of France

[73] Assignees: Adir et Compagnie, Courbevoie; Inserm, Paris, both of France

[21] Appl. No.: 589,797

[22] Filed: Jan. 22, 1996

[30] Foreign Application Priority Data

Jan. 23, 1995 [FR] France ................................. 95 00694

[51] Int. Cl.⁶ ...................................... A61K 38/05
[52] U.S. Cl. ............................... 514/19; 548/535
[58] Field of Search ................. 514/19; 548/535

[56] References Cited

FOREIGN PATENT DOCUMENTS 0723974  7/1996  European Pat. Off. .

*Primary Examiner*—David Lukton
*Attorney, Agent, or Firm*—The Firm of Gordon W. Hueschen

[57] ABSTRACT

Compound of formula (I):

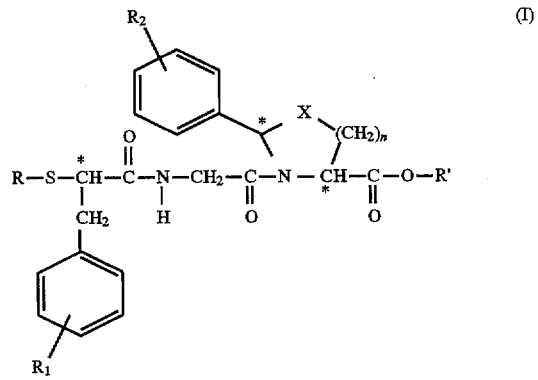

wherein R, $R_1$, $R_2$, R', X and n are as defined in the description, and NEP and ACE inhibitory medicaments containing the same.

14 Claims, No Drawings

MERCAPTOALKANOYLDIPEPTIDE COMPOUNDS

The present invention relates to new mercaptoalkanoyl-dipeptide compounds, mixed inhibitors of neutral endopeptidase (NEP) and angiotensin conversion enzyme (ACE), a process for their preparation and pharmaceutical compositions containing them.

The new dipeptides according to the invention have the remarkable property of inhibiting both neutral endopeptidase (E.C. 3.4–24.11), which causes the inactivation of the auricular natriuretic peptide, and peptidyldipeptidase A (E.C. 3.4–15.1), which generates angiotensin II. They thus behave as mixed inhibitors of neutral endopeptidase (NEP) and peptidyldipeptidase A (ACE), capable of potentiating the natriuretic, diuretic and vasodilatory effects of the auricular natriuretic peptide and of blocking the hypertensive effects caused by angiotensin II.

Numerous products possessing one or the other of those activities are known.

BACKGROUND OF THE INVENTION

The patent specification EP-B-38758 describes products that are inhibitors of the neutral endopeptidase called "encephalinase", since the enzyme degrades encephalins, which are endogenous ligands of morphine receptors. Those inhibitors are consequently useful as analgesics.

Thus, in Nature, 228, (1980), 286–288, B. P. Roques et al. demonstrated that (R,S)-(2- mercaptomethyl-3-phenylpropionyl)glycine (thiorphan) exhibits an inhibitory property at a nanomolar concentration and acts like an analgesic by potentiating the action of encephalins, endogenous opiate peptides.

Other encephalinase inhibitors having analgesic properties form the subject, for example, of the patent specifications FR-B-2 556 721 and EP-B-136 883.

Patent specifications U.S. Pat. No. 4,053,651 and U.S. Pat. No. 4,684,660 describe peptidyldipeptidase A inhibitors, which are useful as anti-hypertensives.

Koehn et al., (J. Bio. Chem., 262, (1987), 11623–11627) and S. L. Stephenson and A. J. Kenny, (Biochem. J., 243, (1987), 183–187) reported that the auricular natriuretic peptide which is released by the heart, especially in the case of cardiac insufficiency, and which increases natriuresis and diuresis and thus exhibits a vasodilatory effect, is inactivated by the peripheral enzyme E.C. 24.11. Thus, the neutral endopeptidase inhibitor, thiorphan, and some of its derivatives are capable of increasing the half-life of the circulating auricular natriuretic peptide and of reducing blood pressure in the rat (G. Olins et al., Mol. Cell. Endocrinol., 61, (1989), 201–208; A. A. Seymour et al., Hypertension, 14, (1989), 87–97). However, none of those known neutral endopeptidase inhibitors has an intrinsic antihypertensive activity and a neutral endopeptidase inhibitor such as thiorphan, in clinical trials, causes natriuresis and diuresis without any significant hypotensive effect and without decreasing cardiac overload.

In the patent specification U.S. Pat. No. 4,879,309, however, compounds of formula:

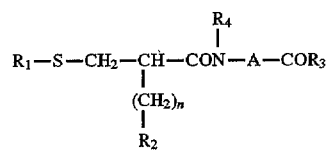

are described, which are useful in increasing natriuresis and diuresis and in reducing blood pressure.

Mixed NEP and ACE inhibitors are described in the patent specifications FR-B-2 682 952 and FR-A-2 679 564. The described compounds have the following formulae:

patent specification FR-B-2 682 952:

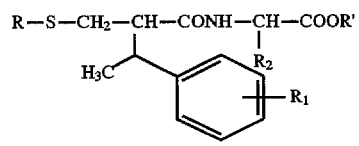

patent specification FR-A-2 679 564:

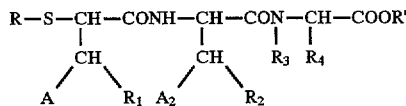

THE PRESENT INVENTION

The present invention relates to new dipeptides that inhibit both neutral endopeptidase and peptidyldipeptidase A at very low concentrations. The compounds according to the invention differ from the compounds of the prior art, especially the patent specifications U.S. Pat. No. 4,879,309 and FR-A-2 679 564, by the fact that all of the compounds of the present invention have in the C-terminal moiety an amino acid having 5 or 6 chain members that is substituted in the 5 or 6 position, respectively, by a phenyl or substituted phenyl radical. Furthermore, that very bulky amino acid imposes the Gly-imino acid chain formation so that an excellent inhibitory activity is obtained on the two enzymes. That type of chain formation results in compounds that exhibit a very powerful inhibitory activity on the two enzymes ($K_I$ of the order of $10^{-9}M$), very long durations of activity and bioavailabilities suitable for blocking both the conversion enzyme to be found for the most part in the vessels, and neutral endopeptidase which degrades the natriuretic peptide, mainly in the proximal renal tubule.

The new compounds according to the invention have the dual property of inhibiting both neutral endopeptidase and peptidyldipeptidase A. As a result, the hypotensive effect obtained with those mixed inhibitors is greater than that obtained with neutral endopeptidase inhibitors and peptidyldipeptidase A inhibitors used on their own or in admixture. In addition, the compounds of the invention exhibit a balanced inhibition of neutral endopeptidase and peptidyldipeptidase A. Indeed the $IC_{50}$ values obtained for a given compound are roughly identical for neutral endopeptidase and peptidyldipeptidase A. This demonstrates the superiority of the compounds of the invention to those of the prior art described in the patent specifications U.S. Pat. No. 4,879,309 and FR-A-2 679 564.

Thus, the compounds of the present invention are very effective in the treatment of congestive cardiac deficiencies and various types of hypertension, and in the treatment of atherosclerosis, cardiac ischaemia, chronic renal deficiencies, and cardiac accidents associated with a pulmonary disorder. They are also effective in reducing side-effects caused by treatment with cyclosporin.

The invention relates more especially to compounds of the general formula (I):

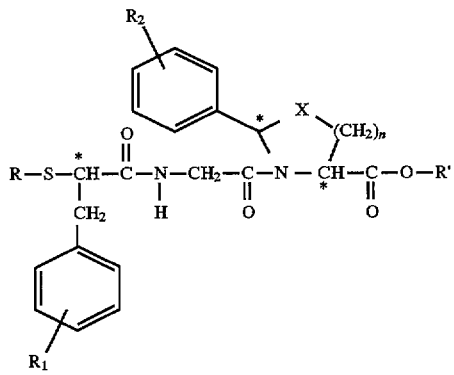

wherein:

—R is selected from hydrogen, an acyl radical containing from 1 to 6 carbon atoms in straight or branched chain, the radicals benzoyl, naphthoyl and adamantoyl and the radical

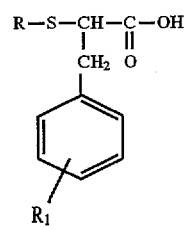

wherein $R_1$, $R_2$, R', X and n are as defined below, $R_1$ and $R_2$, which are identical or different, are each selected, independently of the other, from hydrogen, a hydroxy radical, an alkyl radical containing from 1 to 6 carbon atoms in straight or branched chain, an alkoxy radical containing from 1 to 6 carbon atoms in straight or branched chain, a halogen atom selected from fluorine, chlorine, bromine and iodine, a nitro group, an amino group, a carboxy radical, an alkoxycarbonyl radical containing from 1 to 6 carbon atoms in straight or branched chain, a benzyloxycarbonyloxy radical, a phosphonate radical, a sulphonate radical, the radical $SO_2$—$NH_2$ and the radical $SO_2$—NH-alkyl wherein the term alkyl denotes a saturated hydrocarbon group containing from 1 to 6 carbon atoms in straight or branched chain, R' is selected from hydrogen, an alkyl radical containing from 1 to 20 carbon atoms in straight or branched chain, an aralkyl radical and a cycloalkylalkyl radical, X is selected from oxygen, sulphur, the group $CH_2$ and the group NH, n is selected from the integers 1 and 2, it being understood that:

"aralkyl radical" denotes a radical formed by an aryl group selected from phenyl and naphthyl that is bonded to an alkyl radical containing from 1 to 6 carbon atoms in straight or branched chain, "cycloalkylalkyl radical" denotes a radical formed by a cycloalkyl group containing from 3 to 8 carbon atoms that is bonded to an alkyl radical containing from 1 to 6 carbon atoms in straight or branched chain, and also to their stereoisomeric forms in pure form or in a mixture, and to their possible pharmaceutically acceptable addition salts.

The present invention relates also to a process for the preparation of compounds of formula (I) which is characterised in that the dipeptide of formula (II):

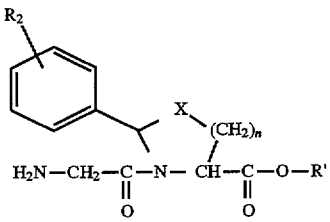

wherein $R_2$, R', X and n are as defined for the compound of formula (I), is subjected to acylation with an acid of formula (III):

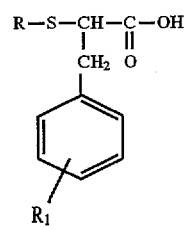

wherein R and $R_1$ are as defined for the compound of formula (I), under the conditions customarily used in peptide synthesis and described, for example, by Bodansky et al. ("Peptide Synthesis", J. Wiley and Sons Edit).

The dipeptides of formula (II) are obtained by condensation of the Z-glycine acyl chloride of formula (IV):

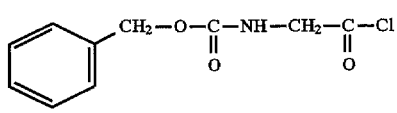

with an ester of formula (V):

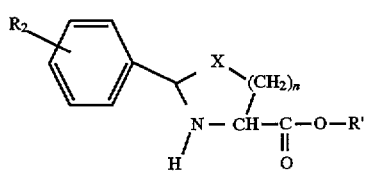

wherein $R_2$, R', X and n are as defined hereinbefore, followed by catalytic hydrogenation.

The compound of formula (II) can be prepared from the corresponding α-amino acid by halogenating deamination according to Fisher et al. (Ann., 357, (1907), 1–24), followed by nucleophilic substitution of the halogen atom.

The compounds of formula (I) can also be obtained by condensation, for example with the aid of Castro's reagent, of compounds of formula (V) with the pseudodipeptides of formula (VI):

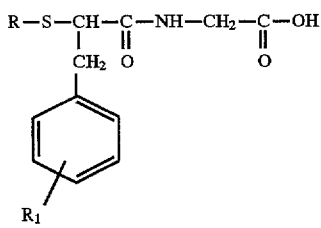

wherein R and $R_1$ are as defined hereinbefore.

The pseudodipeptides of formula (VI) are obtained by the coupling of acids of formula (III) with glycine tert-butyl ester in accordance with conventional methods used in peptide synthesis, followed by deprotection of the acid function with trifluoroacetic acid.

The compounds of formula (V) are obtained according to methods described, for example, by J. N. Barton et al. (*J. Med. Chem.*, 30, (1990), 1606–1615).

The compounds of formula (I) wherein R' represents hydrogen can form pharmaceutically acceptable salts with mineral or organic bases. Among the mineral or organic bases used to form those salts there may be mentioned more especially, and in a non-limiting manner, ammonium, sodium and calcium hydroxides, N-methyl-D-glucamine, lysine, arginine and dicyclohexylamine.

The compounds of the present invention may, where appropriate, exist in the form of pure stereoisomers or in the form of mixtures of stereoisomers. The pure stereoisomers are easily accessible by the one skilled in the art from the mixtures of stereoisomers using classic separation techniques, or asymetric syntheses of the starting materials.

The carbon atoms makred with an asterisk (*) in formula (I) are centres of asymmetry. The present compounds of the present invention are those in which:

the carbon atom carrying the radical

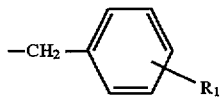

has the S configuration, and
the carbon atom carrying the radical

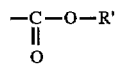

has the S configuration, and
the radicals

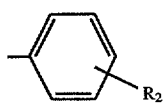

on the one side and

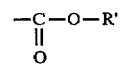

on the other side are located in the cis configuration in relation to the mean plane of the ring.

The Applicant has discovered that the compounds of the invention have very valuable pharmacological properties.

The compounds of the present invention, when administered to mammals, are useful in the treatment and prevention of congestive cardiac deficiencies, essential hypertension, hypertension associated with an increase in blood volume, cardiac and/or renal insufficiency and pulmonary angina, and have a protective effect against thickening of the vascular wall. That results from their dual inhibitory action on neutral endopeptidase and peptidyldipeptidase A. As a result of their pharmacological properties, the compounds of the present invention are also useful in the treatment and prevention of atherosclerosis and cardiac ischaemia. They are also useful in the prevention of hypertrophy, and of fibrosis of the left ventricle and of the pulmonary heart. Patients who have undergone cardiac and/or renal transplants are often treated in the long term with cyclosporin, which has as side-effects an increase in blood pressure and salt retention. The compounds of the invention have properties that oppose those effects and are thus useful in reducing the side-effects caused by cyclosporin.

Peptidyldipeptidase A inhibitors are products known for the treatment of certain hypertensions: they are capable of blocking the increase in blood pressure caused by an increase in vascular resistance and in blood volume resulting from the formation of angiotensin II from angiotensin I.

Another important peptide implicated in the regulation of arterial pressure is the auricular natriuretic peptide released by the heart, which has a vasodilatory property and which is capable of controlling diuresis and natriuresis. The auricular natriuretic peptide is degraded by neutral endopeptidase in peripheral tissues. Neutral endopeptidase inhibitors, such as thiorphan, induce significant diuresis and natriuresis in man without causing an increase in the levels of renin and aldosterone usually observed with the diuretics generally employed in association with ACE inhibitors. The effects of neutral endopeptidase inhibitors on blood pressure when used alone, however, are weak.

The mixed inhibitors of neutral endopeptidase and peptidyldipeptidase A can alleviate human hypertension of various origins and may be used without the coadministration of diuretics and without supplying potassium.

The new products of the present invention are very effective, preventatively and curatively, in the treatment of congestive cardiac deficiencies and various types of hypertension, especially hypertension associated with an increase in blood volume, essential hypertension, atherosclerosis, cardiac ischaemia, cardiac and/or renal insufficiency, cor pulmonale, and pulmonary angina, and have a protective effect against thickening of the vascular wall while protecting bradykinin and the auricular natriuretic peptide from inactivation. They are also effective in reducing side-effects caused by treatment with cyclosporin.

As a result of the dual property of the compounds of the invention of inhibiting both neutral endopeptidase and peptidyldipeptidas A, the hypotensive effect obtained with those mixed inhibitors is greater than that obtained with neutral endopeptidase inhibitors and peptidyldipeptidase A inhibitors used alone or in admixture.

The present invention relates also to pharmaceutical compositions comprising compounds of formula (I), or their stereoisomers in pure form or in the form of a mixture, in the form of the base or pharmaceutically acceptable addition salts, in combination with one or more inert, non-toxic excipients or carriers.

Among the pharmaceutical compositions according to the invention there may be mentioned more especially those which are suitable for oral, parenteral, nasal, rectal, perlingual, ocular or respiratory administration, and especially tablets or dragées, sublingual tablets, sachets, paquets, gelatin capsules, glossettes, lozenges, suppositories, creams, ointments, dermal gels, injectable or drinkable preparations, aerosols, and eye or nose drops.

The choice of the carrier and the levels of active substance in the carrier are generally determined as a function of the solubility and chemical properties of the product, the particular mode of administration and pharmaceutical practice arrangements. For example, excipients such as lactose, sodium citrate, calcium carbonate, dicalcium phosphate and disintegrators such as starch, alginic acids and certain complex silicates associated with lubricants such as magnesium stearate, sodium laurylsulphate and talc, may be used for the preparation of tablets. To prepare a capsule, it is advantageous to use lactose and high-molecular-weight polyethylene glycols. When aqueous suspensions are used, they may contain emulsifiers or agents facilitating suspension. Diluents such as ethanol, propylene glycol, glycerol and chloroform or mixtures thereof may also be used.

There are used for parenteral administration, suspensions or solutions of the products according to the invention in sesame oil, peanut oil or olive oil, or aqueous solutions of propylene glycol as well as sterile aqueous solutions of pharmaceutically acceptable salts. Solutions of salts of the products according to the invention are especially useful for administration by intramuscular or subcutaneous injection. Aqueous solutions, including also solutions of salts in pure distilled water, can be used for intravenous administration provided that their pH is suitably adjusted, that they are judiciously buffered and rendered isotonic with an adequate amount of glucose or sodium chloride, and that they are sterilised by heating or micro-filtration.

The doses used in the methods according to the invention are those which result in a maximum therapeutic effect until an improvement is obtained. Generally, the doses used are those which are therapeutically effective in lowering blood pressure when treating hypertension. In general, the doses administered by the oral route are from 0.1 to 100 mg/kg, preferably from 1 to 10 mg/kg, and those administered by the intravenous route are from 0.01 to 10 mg/kg, preferably from 0.1 to 5 mg/kg, it being understood that in each particular case the doses will be determined as a function of factors peculiar to the patient to be treated, such as age, weight, general state of health and other characteristics that may influence the efficacy of the medicament.

The compounds according to the invention may be administered as frequently as is necessary to obtain the desired therapeutic effect. Some patients may respond rapidly to a more or less strong dose and may be satisfied with much weaker maintenance doses. For other patients, it may be necessary to have treatments spread out at a rate of from 1 to 4 doses per day as a function of the physiological needs of each particular patient. Generally, the active ingredient may be administered orally from 1 to 4 times per day. For other patients it will be necessary to prescribe no more than one or two doses per day.

The compounds of the invention may be used in injectable form in urgent cases of acute hypertension Such a treatment may be followed by an intravenous perfusion of the active ingredient in order to obtain and maintain the desired therapeutic effect.

In the present application, the abbreviations used correspond to the following products:

PyBrOP: bromoxy-tripyrrolidinophosphonium hexafluorophosphate
Cbz: carbobenzoxy (benzyloxycarbonyl)
Z: benzyloxycarbonyl
BOP: benzotriazol-1-yloxy-tris(dimethylamino) phosphonium hexafluorophosphate
DCC: dicyclohexylcarbodiimide

DESCRIPTION OF THE PREFERRED EMBODIMENTS

The following Example illustrate the invention without, however, limiting it in any way. The starting materials are known or are prepared by known methods of operation.

PREPARATION A: N-(2-Acetylthio-3-phenylpropanoyl) glycine tert-butyl ester

A solution of 3.7 g of glycine tert-butyl ester hydrochloride and 3.8 ml of triethylamine in 40 ml of chloroform, a solution of 3 g of 1-hydroxybenzotriazole in 30 ml of tetrahydrofuran and a solution of 6.9 g of DCC in trichloromethane are added in succession to 5 g of 2-acetylthio-3-phenylpropanoic acid dissolved in 40 ml of tetrahydrofuran. After stirring at room temperature for one night, the reaction mixture is filtered and evaporated to dryness. The residue is taken up in ethyl acetate and washed in succession with a 10% citric acid solution, water, 10% sodium hydrogen carbonate solution, water, and a saturated sodium chloride solution, and is then dried over sodium sulphate. After filtration and evaporation to dryness, 7.5 g, of an oil are obtained.

Yield: 98%

$R_f$: 0.65 (n-hexane/ethyl acetate 2:1)

PREPARATION B: N-(2-Acetylthio-3-phenylpropanoyl) glycine 7.5 g of the compound obtained in Preparation A are dissolved in 10 ml of dichloromethane. 17 ml of trifluoroacetic acid are added at 0° C. After 30 minutes at 0° C., the mixture is stirred for 3 hours at room temperature, then evaporated to dryness. The residue is taken up three times in a 50:50 mixture of diethyl ether/n-hexane to yield 6.2 g of an oil corresponding to the expected product.

Yield: 97%

$R_f$: 0.53 (dichloromethane/methanol, 9:1)

PREPARATION C: 2-Acetylthio-3-(para-benzyloxycarbonyioxyphenyl)propanoic acid

A solution of potassium thioacetate (prepared from 2.5 ml of thioacetic acid and 2 g of potassium carbonate in water) is added to 10 g of 2-bromo-3-(para-benzyloxycarbonyloxyphenyl)propanoic acid (prepared in accordance with K. Koga et al. Chem. Pharm. Bull., 26, 178 (1978)) dissolved in 1M sodium hydroxide. The mixture is stirred for 2 days at room temperature. After acidification with 1N hydrochloric acid, the aqueous phase is extracted three times with ethyl acetate, washed with a saturated sodium chloride solution and dried over sodium sulphate. After filtration and evaporation to dryness a yellow oil is obtained which is purified by chromatography on silica gel (eluant: n-hexane/ethyl acetate/acetic acid 8:2:0.5). 6.4 g of an oily product are obtained.

Yield :65%

$R_f$: 0.49 (n-hexane/ethyl acetate/acetic acid, 6:4:0.5).

PREPARATION D: N-[2-Acetylthio-3-(para-benzyloxcarbonyioxyphenyl)propanoyl]-glycine tert-butyl ester 1.6 g of the compound obtained in Preparation C are condensed under the conditions of Preparation A with 0.72 g of glycine tert-butyl ester. 2 g of a pale yellow oil are obtained.

Yield: 96%

$R_f$: 0.57 (hexane/ethyl acetate, 1:1)

PREPARATION E: N-[2-Acetylthio-3-(para-benzyloxycarbonyloxyphenyl)propanoyl]glycine 2 g of the compound obtained in Preparation D are treated under the conditions of Preparation B. After chromatography on silica gel in a hexane/ethyl acetate/acetic acid mixture, 4:6:0.5, 1.35 g of an oil is obtained which slowly crystallises.

Yield: 76%

$R_f$: 0.25 (hexane/ethyl acetate/acetic acid, 4:6:0.5).

PREPARATION F: 2-Acetylthio-3-(para-nitrophenyl) propanoic acid 2.7 g of 2-bromo-3-(para-nitrophenyl)propanoic acid (prepared from (para-nitrophenyl)alanine) are added at 0° C., under nitrogen, to a solution of sodium thioacetate (prepared from 0.73 g of sodium hydride and 1.05 ml of thioacetic acid) in dimethylformamide. After stirring for 48 hours at room temperature, then evaporating to dryness and taking up the residue in water, the mixture is treated as described in Preparation C. 2.3 g of a pale yellow oil are obtained.

Yield: 88%

$R_f$: 0.63 (dichloromethane/methanol/acetic acid, 9:1:0.2)

PREPARATION G: N-Glycyl-5-(meta-hydroxyphenyl) proline methyl ester

Step a: N-[(N-Cbz)-glycyl]-5-(meta-hydroxyphenyl) proline methyl ester 0.6 g of Z-glycine dissolved in dichloromethane is coupled with 0.83 g of 5-(meta-hydroxyphenyl)proline methyl ester in the presence of 2.06 g of PyBrOP and 2.6 ml of diisopropylethylamine. After stirring for 4 hours at room temperature, the organic phase is washed (sodium hydrogen carbonate, water, citric acid, water), dried over sodium sulphate, filtered and evaporated to dryness. The oily residue is chromatographed on silica gel (n-hexane/ethyl acetate. 4:6). A white solid corresponding to the expected product is obtained.

Yield: 33%

Melting point: 173° C.

$R_f$: 0.17 (n-hexane/ethyl acetate, 4:6)

Step b: N-Glycyl-5-(meta-hydroxyphenyl)proline methyl ester 0.39 g of the compound obtained in Step a is hydrogenated at room temperature and normal pressure in the presence of 10% palladium-on-carbon and 1 equivalent of 1N hydrochloric acid dissolved in methanol. After stirring for 3 hours at room temperature, the catalyst is filtered off and the solvent is evaporated to dryness.

Yield: 100%

PREPARATION H: N-[(N-Cbz)-glycyl]-5-(para-methylphenyl)proline methyl ester 1 equivalent of Z-glycine dissolved in acetone is treated with cyanuric chloride in the presence of triethylamine. After stirring for 3 hours at room temperature, the mixture is evaporated to dryness. The residue is taken up in carbon tetrachloride and 1 equivalent of 5-(para-methylphenyl) proline methyl ester is added in solution in dichloromethane and in the presence of triethylamine. After stirring for 3 hours at room temperature, the reaction mixture is evaporated to dryness, taken up in ethyl acetate, washed, dried, and evaporated to dryness again. The oily residue so obtained is chromatographed in an n-hexane/ethyl acetate mixture, 1:1, to yield a white solid.

Yield: 41%

$R_f$: 0.18 (n-hexane/ethyl acetate, 1:1)

PREPARATION I: N-[(N-Cbz)-glycyl]-5-(ortho-methylphenyl)proline methyl ester

This compound is obtained from Z-glycine and 5-(ortho-methylphenyl)proline methyl ester in accordance with the process described in Preparation H. The oily product so obtained is purified by chromatography in an n-hexane/ethyl acetate mixture, 55:45, to yield a colourless oil.

Yield: 42%

$R_f$: 0.21 (n-hexane/ethyl acetate, 1:1)

EXAMPLE 1: N-[N-(2-Acetylthio-3-phenylpropanoyl) glycyl]-5-phenylproline tert-butyl ester A solution of 5.4 g of 5-phenylproline tert-butyl ester and 3.35 ml of triethylamine in 40 ml of trichloromethane, a solution of 2.96 g of 1-hydroxybenzotriazole in 30 ml of tetrahydrofuran and a solution of 6.76 g of DCC in 30 ml of trichloromethane are added in succession at 0° C. to 6.1 g of the compound obtained in Preparation B dissolved in 40 ml of tetrahydrofuran. The reaction mixture is treated as described in Preparation A. The crude product is purified by chromatography on silica gel with a hexane/ethyl acetate mixture, 2:1, as eluant. 6.47 g of an oily compound are obtained.

Yield: 60%

$R_f$: 0.49 (ethyl acetate/hexane, 1:1)

EXAMPLE 2: N-[N-(2-Acetylthio-3-phenylpropanoyl)-glycyl]-5-phenylproline 5 ml of trifluoroacetic acid are added at 0° C. to a solution of 3.2 g of the compound obtained in Example 1 in 10 ml of dichloromethane. The mixture is stirred for 30 minutes at 0° C., then for 2 hours 30 minutes at room temperature. After evaporation to dryness, the oily residue precipitates in an ether/hexane mixture, 1:1.1.66 g of a white solid are obtained.

Yield: 58.5%

$R_f$: 0.57 (dichloromethane/methanol, 9:1)

EXAMPLE 3: N-[N-(2-Mercapto-3-phenylpropanoyl) glycyl]-5-phenylproline 0.700 g of the compound obtained in Example 2 is dissolved in 10 ml of degassed methanol. 5 ml of a degassed 1M sodium hydroxide solution are added at 0° C. and the mixture is stirred for 1 hour at 0° C. and then for 3 hours at room temperature. The mixture is acidified with 1M hydrochloric acid until a pH of 1 is reached and is concentrated in vacuo. The residue is taken up in water and the aqueous phase is extracted with ethyl acetate. The organic phase is washed with water, with a saturated sodium chloride solution, then dried over sodium sulphate. After filtration and evaporation to dryness, 610 mg of a pale yellow oil are obtained which slowly crystallises.

Yield: 96%

Melting Point: 75° C.

$R_f$: 0.24 (dichloromethane/methanol, 95:5)

EXAMPLE 4: N-[N-(2-Acetylthio-3-phenylpropanoyl) glycyl]-5-(ortho-hydroxyphenyl)-proline methyl ester 0.500 g of the compound obtained in Preparation B and 0.400 g of 5-(ortho-hydroxyphenyl)-proline methyl ester are condensed under the conditions of Example 1. After chromatography on silica gel with a hexane/ethyl acetate mixture, 6:4, 0.32 of the expected product is obtained in the form of an oil.

Yield: 50%

$R_f$: 0.2 (cyclohexane/ethyl acetate, 1:1)

EXAMPLE 5: N-[N-(2-Mercapto-3-phenylpropanoyl) glycyl]-5-(ortho-hydroxyphenyl)-proline 0.300 g, of the compound obtained in Example 4 is treated as described in Example 3. 0.200 g of the expected compound is obtained.

Yield: 88%

$R_f$: 0.69 (dichloromethane/methanol/acetic acid, 9: 1:0.5)

EXAMPLE 6: N-[N-[2-Acetylthio-3-(para-benzyloxycarbonyloxyphenyl)propanoylglycyl-5-(ortho-hydroxyphenyl)proline methyl ester 0.65 of 5-(ortho-hydroxyphenyl)proline methyl ester, 0.7 ml of diisopropylethylamine and 1.27 g of BOP are added at 0° C. to a solution of 0.500 g of the compound obtained in Preparation E in dichloromethane. Stirring is maintained at room temperature for 48 hours. After treatment in accordance with conventional conditions, the oil obtained is purified by chromatography in a hexane/ethyl acetate mixture, 4:6. 0.35 g of an oily product is obtained.

Yield: 47%

$R_f$: 0.53 (cyclohexane/ethyl acetate/acetic acid, 3:7:0.2)

EXAMPLE 7 : N-[N-[2-Mercapto-3-(para-hydroxyphenyl)propanoyl]glycyl]-5-(ortho-hydroxyphenyl)proline 2 ml of degasses 1M sodium hydroxide are added at 0° C. to 0.200 g of the compound obtained in Example 6 in 1 ml of degasses methanol. After stirring for 1 hour at 0° C. then for 2 hours at room temperature, the reaction mixture is treated as described in Example 3. 0.125 g of a white solid is obtained.

Yield: 89%

$R_f$: 0.34 (dichloromethane/methanol/acetic acid, 9:1:0.2)

EXAMPLE 8: N-[N-[2-Acetylthio-3-(para-benzyloxycarbonyloxyphenyl)propanoyl]-glycyl]-5-phenylproline tert-butyl ester 0.590 g of the compound obtained in Preparation C is condensed with Gly-(5-phenyl)-Pro dipeptide tert-butyl ester under the conditions of Preparation A. 1 g of the expected compound is obtained.

Yield: 98%

$R_f$: 0.46 (hexane/ethyl acetate, 1:2)

EXAMPLE 9: N-[N-[2-Acetylthio-3-(para-hydroxyphenyl) propanoyl]glycyl]-5-phenylproline 1 g of the compound obtained in Example 8 is dissolved in a mixture of boron tris(trifluoroacetate) and trifluoroacetic acid under nitrogen at 0° C. The mixture is stirred at the same temperature for 20 minutes. After evaporation to dryness, the residue is taken up 3 times in methanol and evaporated to dryness again. The oily residue then precipitates in diethyl ether thus yielding 710 g of a pale yellow powder.

Yield: 75%

$R_f$: 0.71 (dichloromethane/methanol/acetic acid, 9:1:0.5)

EXAMPLE 10: N-[N-[2-Mercapto-3-(para-hydroxyphenyl)propanoyl]glycyl]-5-phenylproline 450 mg of the compound obtained in Example 9 are dissolved in 5 ml of degassed methanol. 2 ml of 1M sodium hydroxide are added at 0° C., and the reaction is continued as described in Example 3. 400 mg of the expected compound are obtained in the form of a white solid.

Yield :97%

$R_f$: 0.83 (trichloromethane/methanol/acetic acid, 7:3:0.5)

EXAMPLE 11: N-[N-[2-Acetylthio-3-(para-nitrophenyl)propanoyl]glycyl]-5-phenyl-proline tert-butyl ester By reacting 1 g of the compound obtained in Preparation F and 1.15 g of N-glycyl-5phenylproline tert-butyl ester under the conditions described in Example 1, an oily compound is obtained which is purified by chromatography on silica gel in a cyclohexane/ethyl acetate mixture, 1:1 1.09 g of a pale yellow oil are obtained.

Yield : 53%

EXAMPLE 12: N-[N-[2-Acetylthio-3-(para-nitrophenyl)propanoyl]glycyl]-5-phenylproline 2 ml of trifluoroacetic acid are added at 0° C. to 0.72 g, of the compound obtained in Example 11 dissolved in 2 ml of dichloromethane. After treatment under the conditions described in Example 2. 0.58 g of a white solid is obtained.

Yield: 90%

$R_f$: 0.39 (dichloromethane/methanol, 9:1)

EXAMPLE 13: N-[N-[2-Acetylthio-3-(para-aminophenyl) propanoyl]glycyl]-5-phenylproline 300 mg of the compound obtained in Example 12 are dissolved in 15 ml of methanol and a few drops of acetic acid, then the mixture is hydrogenated under normal pressure in the presence of palladium-on-carbon. After filtration of the catalyst and evaporation of the solvent 0.280 g of a white solid is obtained.

Yield: 100%

$R_f$: 0.31 (dichloromethane/methanol/acetic acid 9:1:0.25)

EXAMPLE 14: N-[N-[2-Mercapto-3-(para-aminophenyl) propanoyl]glycyl]-5-phenylproline 0.150 g of the compound obtained in Example 13 is treated under the conditions of Example 3. After customary treatment of the organic phase, 0.103 g of a white solid is obtained.

Yield: 89%

$R_f$: 0.36 (dichloromethane/methanol/acetic acid, 9: 1:0.3)

EXAMPLE 15: N-[N-[2-Acetylthio-3-(para-benzyloxycarbonyioxyphenyl)propanoyl]glycyl]-5-(para-aminophenyl)proline methyl ester The compound of Preparation E is coupled with 5-(para-aminophenyl)proline methyl ester in accordance with the conditions described in Example 6. An oily product is obtained which is chromatographed in a dichloromethane/methanol/acetic acid mixture, 15:0.4:0.1. A white foamy product is obtained.

Yield: 35%

$R_f$: 0.25 (dichloromethane/methanol/acetic acid, 9:1:0.25)

EXAMPLE 16: N-[N-[2-Mercapto-3-(para-hydroxyphenyl) propanoyl]glycyl]-5-(para-aminophenyl)proline The compound obtained in Example 15 is treated in accordance with the conditions of Example 7. A white solid corresponding to the expected product is obtained.

Yield: 60%

$R_f$: 0.37 (dichloromethane/methanol/acetic acid, 9: 1:0.5)

EXAMPLE 17: N-[N-[2-Acetylthio-3-(para-benzyloxycarbonyloxyphenyl)propanoyl]glycyl]-5-(meta-hydroxyphenyl)proline methyl ester 0.35 g of the compound obtained in Preparation C is coupled with 0.3 g of the compound obtained in Preparation G in accordance with the process described in Preparation A. An oily product is obtained which is chromatographed on silica gel in a hexane/ethyl acetate mixture, 4:6. 0.24 g of the expected product is obtained.

Yield : 40%

$R_f$: 0.37 (n-hexane/ethyl acetate, 4:6)

EXAMPLE 18: N-[N-[2-Mercapto-3-(para-hydroxyphenyl) propanoyl]glycyl]-5-(metahydroxyphenyl)proline 0.24 g of the compound obtained in Example 17 is dissolved in degassed methanol, then treated with 4 equivalents of a degassed aqueous 1N sodium hydroxide solution. After stirring for 30 minutes at 0° C. and for 2 hours at room temperature, the reaction mixture is acidified and extracted with ethyl acetate. After evaporation to dryness, 0.12 g of a white solid is obtained.

Yield: 71%

$R_f$: 0.34 (dichloromethane/methanol/acetic acid, 9:1:0.5)

EXAMPLE 19: N-[N-(2-Acetylthio-3-phenylpropanoyl) glycyl]-5-(meta-hydroxyphenyl)-proline methyl ester The compound obtained in Preparation G is coupled with 2-acetylthio-3-phenylpropanoic acid in accordance with the process described in Preparation A. An oily product is obtained which is chromatographed in a mixture of n-hexane/ethyl acetate, 1:1.

Yield: 50%

$R_f$: 0.28 (n-hexane/ethyl acetate, 4:6)

EXAMPLE 20: N-[N-(2-Mercapto-3-phenylpropanoyl) glycyl]-5-(meta-hydroxyphenyl)proline The compound obtained in Example 19 is treated in accordance with the process of Example 3. A pasty product corresponding to the expected compound is obtained.

Yield: 85%

$R_f$: 0.29 (dichloromethane/methanol/acetic acid, 9:0.5:0.25)

EXAMPLE 21: N-[N-[2-Acetylthio-3-(para-benzyloxycarbonyloxyphenyl)propanoyl]glycyl]-5-(para-hydroxyphenyl)proline methyl ester The compound obtained in Preparation C is coupled with N-glycyl-5-(para-hydroxyphenyl)proline methyl ester, prepared in accordance with the processes described in Steps a and b of Preparation G. An oily product corresponding to the expected compound is obtained.

Yield : 50%

$R_f$: 0.26 (cyclohexane/ethyl acetate/acetic acid, 5.5:4.5:0.5)

EXAMPLE 22: N-[N-[2-Mercapto-3-(para-hydroxyphenyl) propanoyl]glycyl]-5.(para-hydroxyphenyl)proline The compound of Example 21 is treated in accordance with the process described in Example 3. A pasty product is obtained.

Yield: 77%

$R_f$: 0.24 (dichloromethane/methanol/acetic acid, 9:1:0.5)

EXAMPLE 23: N-[N-[2-Acetylthio-3-(para-chlorophenyl) propanoyl]glycyl]-5-(ortho-hydroxyphenyl)proline methyl ester Condensation of 2-acetylthio-3-(para-chlorophenyl) propanoic acid with N-glycyl-5-(ortho-hydroxyphenyl) proline methyl ester, obtained in accordance with the same protocols as those described in Preparation G, yields the expected product in the form of an oil after chromatography in an n-hexane/ethyl acetate mixture, 1:1.

Yield: 53%

$R_f$: 0.38 (n-hexane/ethyl acetate, 4:6)

EXAMPLE 24: N-[N-[2-Mercapto-3-para-chlorophenyl) propanoyl]glycyl]-5-(ortho-hydroxyphenyl)proline The compound obtained in Example 23 is treated in accordance with the process described in Example 3. A pasty white solid is obtained.

Yield: 88%

$R_f$: 0.26 (dichloromethane/methanol/acetic acid, 9:0.5:0.25)

EXAMPLE 25: N-[N-[2-Acetylthio-3-(para-methoxyphenyl)propanoyl]glycyl]-5(ortho-hydroxyphenyl) proline methyl ester Condensation of 2-acetylthio-3-(para-methoxyphenyl) propanoic acid with N-glycyl-5-(ortho-hydroxyphenyl) proline methyl ester, obtained in accordance with the same protocols as those described in Preparation G, yields the expected product in the form of an oil after chromatography in an n-hexane/ethyl acetate mixture, 4:6.

Yield:50%

$R_f$: 0.28 (n-hexane/ethyl acetate, 4:6)

EXAMPLE 26: N-[N-[2-Mercapto-3-(para-methoxyphenyl) propanoyl]glycyl]-5-(orthohydroxyphenyl)proline By treatment of the compound obtained in Example 25 in accordance with the conditions described in Example 3, a while solid is obtained.

Yield: 88%

$R_f$: 0.42 (dichloromethane/methanol/acetic acid, 9:0.5:0.25)

EXAMPLE 27: N-[N-[2-Acetylthio-3-(para-methoxyphenyl)propanoyl]glycyl]-5-(ortho-methoxyphenyl)proline methyl ester Condensation of 2-acetylthio-3-(para-methoxyphenyl) propanoic acid with N-glycyl-5-(ortho-methoxyphenyl) proline methyl ester, obtained in accordance with the same protocols as those decribed in Preparation G, yields the expected product in the form of a white solid after chromatography in an n-hexane/ethyl acetate mixture, 1:1.

Yield: 59%

$R_f$: 0.26 (n-hexane/ethyl acetate, 4:6)

EXAMPLE 28 : N-[N-[2-Mercapto-3-(para-methoxyphenyl)propanoyl]glycyl]-5-(orthomethoxyphenyl) proline Treatment of the compound obtained in Example 27 in accordance with the conditions of Example 3 yields a white solid.

Yield: 89%

$R_f$: 0.22 (cyclohexane/ethyl acetate/acetic acid, 5:5:0.5)

EXAMPLE 29: N-[N-(2-Acetylthio-3-phenylpropanoyl) glycyl]-5-(para-methylphenyl)proline methyl ester The compound obtained in Preparation H is deprotected in accordance with the process described in Step b of Preparation G; the dipeptide obtained is coupled with 2-acetylthio-3phenylpropanoic acid in accordance with the process described in Preparation A. The oily product so obtained is chromatographed in an n-hexane/ethyl acetate mixture, 5.5:4.5, to yield a white solid.

Yield: 60%

$R_f$: 0.55 (n-hexane/ethyl acetate, 4:6)

EXAMPLE 30: N-[N-(2-Mercapto-3-phenylpropanoyl) glycyl]-5-(para-methylphenyl)proline The compound obtained in Example 29 is treated in accordance with the process described in Example 3. A white solid is obtained.

Yield: 89%

$R_f$: 0.59 (dichloromethane/methanol/acetic acid, 9:0.5:0.5)

EXAMPLE 31: N-[N-[2-Acetylthio-3-(para-hydroxyphenyl)propanoyl]glycyl]-5-(para-methylphenyl) proline methyl ester The compound obtained in Preparation H is deprotected in accordance with the process described in Step b of Preparation G; the dipeptide obtained is coupled with the compound obtained in Preparation C in accordance with the process described in Preparation A. The oily product so obtained is chromatographed in an n-hexane/ethyl acetate mixture, 1:1, to yield a white solid.

Yield: 52%

$R_f$: 0.14 (n-hexane/ethyl acetate, 1:1)

EXAMPLE 32: N-[N-[2-Mercapto-3-(para-hydroxyphenyl) propanoyl]glycyl]-5-(para-methylphenyl)proline The compound obtained in Example 31 is treated in accordance with the process described in Example 3. A white solid is obtained.

Yield: 92%

$R_f$: 0.60 (dichloromethane/methanol/acetic acid, 9:1:0.5)

EXAMPLE 33: N-[N-[2-Acetylthio-3-(para-hydroxyphenyl)propanoyl]glycyl]-5-(ortho-methylphenyl) proline methyl ester The compound obtained in Preparation I is deprotected in accordance with the process described in Step b of Preparation G and the dipeptide obtained is coupled with the compound obtained in Preparation C in accordance with the process described in Preparation A. The oily product so obtained is purified by chromatography in an n-hexane/ethyl acetate mixture, 1:1, to yield an oil.

Yield: 56%

$R_f$: 0.28 (n-hexane/ethyl acetate, 4:6)

EXAMPLE 34: N-[N-[2-Mercapto-3-(para-hydroxyphenyl) propanoyl]glycyl]-5-(ortho-methylphenyl)proline The compound obtained in Example 33 is treated in accordance with the process of Example 3. A white solid is obtained.

Yield: 87%

Melting point: 130° C. (decomposition)

$R_f$: 0.24 (n-hexane/ethyl acetate 4:6)

EXAMPLE 35: N-[N-(2-Acetylthio-3-phenylpropanoyl) glycyl]-5-(ortho-methylphenyl)proline methyl ester The compound obtained in Preparation I is deprotected in accordance with the process described in Step b of Preparation G and the dipeptide obtained is coupled with 2-acetylthio-3-phenylpropanoic acid in accordance with the process of Preparation A. The white solid so obtained is chromatographed in an n-hexane/ethyl acetate mixture, 55:45.

Yield: 58%

Melting point: 97° C.

$R_f$: 0.40 (n-hexane/ethyl acetate, 4:6)

EXAMPLE 36: N-[N-(2-Mercapto-3-phenylpropanoyl) glycyl]-5-(ortho-methylphenyl)proline The compound obtained in Example 35 is treated in accordance with the process of Example 3. A white solid is obtained.

Yield : 63%

Melting point: 110° C. (decomposition)

$R_f$: 0.15 (dichloromethane/methanol/acetic acid, 9:0.7:0.25)

Using analogous processes, the compounds of the following Examples are obtained:

EXAMPLE 37: N-[N-(2-Propanoylthio-3-phenylpropanoyl) glycyl]-5-(ortho-hydroxyphenyl)proline EXAMPLE 38: N-[N-(2-Benzoylthio-3-phenylpropanoyl) glycyl]-5-phenylproline EXAMPLE 39: N-[N-[2-Mercapto-3-(para-sulphamoylphenyl)propanoyl]glycyl]-5phenylproline EXAMPLE 40: N-[N-[2-Mercapto-3-(para-propylsulphamoylphenyl)propanoyl]glycyl]5-(meta-hydroxyphenyl)proline EXAMPLE 41: N-[N-[2-Acetylthio-3-(para-sulphamoylphenyl)propanoyl]glycyl]-5-(meta-hydroxyphenyl)proline cyclohexylmethyl ester EXAMPLE 42: N-[N-[2-Mercapto-3-(para-hydroxyphenyl) propanoyl]glycyl]-5-(meta-hydroxyphenyl)proline benzyl ester EXAMPLE 43: N-[N-[2-Mercapto-3-(para-chlorophenyl) propanoyl]glycyl]-2-(orthohydroxyphenyl)imidazolidine-5-carboxylic acid EXAMPLE 44: N-[N-(2-Mercapto-3-phenylpropanoyl) glycyl]-2-phenyloxazolidine-5-carboxylic acid EXAMPLE 45: N-[N-(2-Mercapto-3-phenylpropanoyl) glycyl]-2-(ortho-hydroxyphenyl)-thiazolidine-5-carboxylic acid EXAMPLE 46: N-[N-[2-Mercapto-3-(para-hydroxyphenyl) propanoyl]glycyl]-2-(meta-hydroxyphenyl) hexahydropyrimidinyl-6-carboxylic acid EXAMPLE 47: N-[N-(5R)-[(2S)-2-mercapto-3-(para-hydroxyphenyl)propanoyl]glycyl]5-(meta-hydroxyphenyl)-L-proline The (5R)-5-(meta-hydroxyphenyl)-L-proline, obtained according to the preparation process described by J. Ezquerra et al. (Tetrahedron Letters, 34 (39), (1993), 6317–6320), is treated under the conditions described in Preparation G, and coupled, according to the process described in Preparation A, with (2S)-2-acetylthio-3-(para-benzyloxycarbonyloxyphenyl)propanoic acid obtained in Preparation C. The so obtained ester is saponified as described in Example 18 to yield the title compound. Compounds of Examples 48 to 53 are similarly obtained as described in Example 47.

EXEMPLE 48: N-[N-(5R)-[(2S)-(2-mercapto-3-phenylpropanoyl)glycyl]-5-phenyl]-L-proline EXEMPLE 49 : N-[N-(5R)-[(2S)-(2-mercapto-3-phenylpropanoyl)glycyl]-5-(ortho-hydroxyphenyl)]-L-proline EXEMPLE 50: N-[N-(5R)-[(2S)-[2-mercapto-3-(para-chlorophenyl)propanoyl]glycyl]-5(ortho-hydroxyphenyl)-L-proline EXEMPLE 51: N-[N-(5R)-[(2S)-[2-mercapto-3-(para-aminophenyl)propanoyl]glycyl]-5phenyl]-L-proline EXEMPLE 52: N-[N-(5S)-[(2S)-2-mercapto-3-(para-hydroxyphenyl)propanoyl]glycyl]5-(meta-hydroxyphenyl]-D-proline EXEMPLE 53: N-[N-(5R)-[(2R)-2-mercapto-3-(para-hydroxyphenyl)propanoyl]glycyl]5-(meta-hydroxyphenyl]-L-proline EXEMPLE 54: N-[N-(5S)-[(2S)-2-mercapto-3-(para-hydroxyphenyl)propanoyl]glycyl]-5-(meta-hydroxyphenyl]-L-proline Step a: (2S)-5-(meta-hydroxyphenyl)-3,4-dihydro[2H] pyrrole-2-carboxylic acid Compound obtained according to the protocol described by Gershon et al. (J. Med. Chem., (1965), 8, 877–881).

Step b: (5S)-5-(meta-hydroxyphenyl)-L-proline

The compound obtained in Step a is reduced (treatment by $OH^-$, $H^+$ and $NaBH_4$) so as to yield a mixture of (2S, 5R) and (2S, 5S) isomers, which are then separated according to the process described by C. G. Overberger et al. (Macromolecules, (1972), 5 (4), 368–372).

Step c : N-[N-(5S)-[(2S)-2-mercapto-3-para-hydroxyphenyl)propanoyl]glycyl]-5(meta-hydroxyphenyl]-L-proline The title compound is obtained from the compound obtained at the preceding Step according to the preparation process described in Example 47.

EXAMPLE 55: N-[N-(5R)-[(2S)-2-mercapto-3-(para-hydroxyphenyl)propanoyl]glycyl]-5-(meta-hydroxyphenyl] -L-proline Compound obtained according to the preparation process described in Example 54, starting from (2R)-5-(meta-hydroxyphenyl)-3,4-dihydro[2H]pyrrole-2-carboxylic acid.

PHARMACOLOGICAL STUDY

EXAMPLE A: Inhibitory effect in vitro on neutral endopeptidase (NEP) and peptidyl-dipeptidase A (ACE)

The inhibitory properties of the compounds of the invention are measured using [$^3$H]-D-Ala$^2$-Leu-encephalin as substrate for neutral endopeptidase, in accordance with the protocol described by Llorens et al. (Biochem. Biophys. Res. Commun., 96, (1980), 1710 sqq), and Z-Phe-His-Leu as substrate in the case of peptidyldipeptidase A in accordance with the protocol described in Biochem. Biophys. Acta, 206, (1970), 136–142.

The results are given in Table I, which also gives the results obtained with N-(2- mercaptomethyl-3-phenyl-1-oxopropyl)glycine (thiorphan) which, although of very similar structure, exhibits an activity on neutral endopeptidase (NEP) only.

TABLE I

Inhibitory effect on neutral endopeptidase (NEP) and angiotensin conversion enzyme (ACE)

| COMPOUND | IC$_{50}$(nM) NEP | IC$_{50}$(nM) ACE |
|---|---|---|
| Example 3 | 1.6 ± 0.3 | 0.55 ± 0.05 |
| Example 5 | 1.1 ± 0.3 | 0.50 ± 0.10 |
| Example 7 | 4.3 ± 0.3 | 0.35 ± 0.05 |
| Example 10 | 3.4 ± 0.8 | 4.2 ± 0.4 |
| Example 14 | 1.8 ± 0.4 | 3.5 ± 0.5 |
| Example 16 | 26 ± 3 | 23 ± 3 |
| Example 18 | 1.6 ± 0.3 | 0.7 ± 0.2 |
| Example 20 | 2.4 ± 0.8 | 1.4 ± 0.7 |
| Example 22 | 6 ± 1 | 0.45 ± 0.05 |
| Example 24 | 1.2 ± 0.4 | 0.90 ± 0.06 |
| Example 26 | 2.3 ± 0.3 | 0.40 ± 0.05 |
| Example 28 | 2.5 ± 0.6 | 2.20 ± 0.20 |
| Example 30 | 10 ± 2 | 8.2 ± 0.5 |
| Example 32 | 5.0 ± 0.5 | 3.2 ± 0.4 |
| Example 34 | 3.1 ± 0.3 | 5.2 ± 0.5 |
| Example 36 | 4.0 ± 0.6 | 3.5 ± 0.6 |
| thiorphan | 2.0 ± 0.4 | 140 ± 13 |

EXAMPLE B: Inhibitory effect in vivo on renal neutral endopeptidase (NEP) and pulmonary peptidyldipeptidase A (ACE)

The compounds are administrated per os to mice in a single dose. Inhibition of both enzymes is measured during a time period from 1 hour to 16 hours by competitive experiments with specific radiolabelled markers for each enzyme. After i.v. administration of a radiolabelled ACE inhibitor ([$^3$H]trandolaprilate) or a radiolabelled NEP inhibitor ([$^3$H]HACBOGIy), the animal is sacrificed and the lungs or the kidneys are removed. The organs are homogenized and the radioactivity associated to these homogenates is measured by liquid scintillation as described in the protocol by M. C. Fournié-Zaluski et al. (*J. Med. Chem.*, 37, (1994), 1070–1083).

By way of example, the compound described in Example 47 has provided the results shown in the following Table II:

TABLE II

Inhibition in vivo of renal NEP and pulmonary ACE
(Compound of Example 47: dose administered p.o.:
2.6 × 10$^{-6}$ mol/kg, that is 1.5 mg/kg)

| time elapsed after administration | % inhibition | |
|---|---|---|
| | renal NEP | pulmonary ACE |
| 1 h | 75 ± 3 | 90 ± 1 |
| 2 h | 70 ± 5 | 86 ± 3 |
| 4 h | 74 ± 4 | 87 ± 3 |
| 8 h | 60 ± 10 | 73 ± 3 |
| 16 h | 48 ± 4 | 20 ± 8 |

EXAMPLE C: Anti-hypertensive effects

The anti-hypertensive effect of the compounds of the invention is determined in vivo in the rat affected by a hypertension induced by the administration of DOCA salt (deoxycorticosterone acetate) and in the spontaneously hypertensive male rat (SHR), in accordance with the protocol described by Trapani et al. (*J. Cardiovasc. Pharmacol.*, 14, (1989), 419–424). In that test the compounds of the invention are shown to be powerful anti-hypertensives and to be non-toxic.

By way of example, the compound described in Example 47 has provided, for the SHR rat, the results shown in the following Table III:

TABLE III

Study of the anti-hypertensive effect in the SHR rat
(Administration p.o., single dose of 25 mg/kg/day;
the animals are treated during 6 days,
first administration Day 1, last administistration Day 6)

| | Systolic blood pressure (mm Hg) | |
|---|---|---|
| DAY | Treated animals (n = 10) | Control animals (n = 10) |
| 0 | 210 ± 5 | 210 ± 5 |
| 1 | 212 ± 3 | 195 ± 3* |
| 2 | 211 ± 1 | 189 ± 5* |
| 3 | 210 ± 2 | 183 ± 4* |
| 4 | 205 ± 2 | 184 ± 3* |
| 5 | 205 ± 1 | 182 ± 3* |
| 6 | 213 ± 2 | 185 ± 5* |
| 7 | 209 ± 4 | 189 ± 3 |
| 8 | 212 ± 2 | 198 ± 5 |
| 9 | 208 ± 2 | 203 ± 5 |
| 10 | 214 ± 1 | 210 ± 3 |

□*:p < 0.01 treatment

EXAMPLE D: Pharmaceutical composition: tablets

Formulation for the preparation of 1000 tablets each comprising 10 mg of active ingredient

| | |
|---|---|
| compound of Example 5 | 10 g |
| lactose | 50 g |
| magnesium stearate | 10 g |
| wheat starch | 20 g |
| corn starch | 10 g |
| silica | 5 g |
| hydroxypropyl cellulose | 5 g |

We claim:

1. A compound selected from those of formula (I):

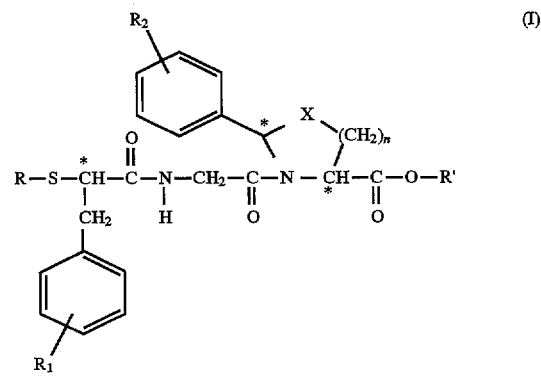

wherein:

R is selected from hydrogen, acyl having 1 to 6 carbon atoms inclusive in straight or branched chain, benzoyl, naphthoyl, and adamantoyl and

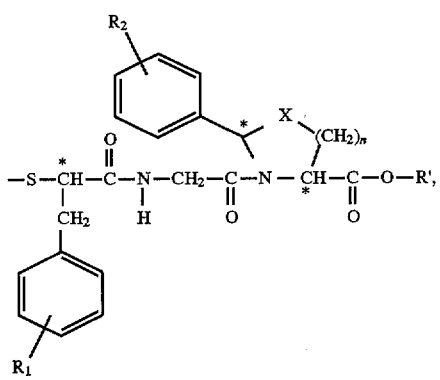

wherein $R_1$, $R_2$, R', X and n are as defined below, $R_1$ and $R_2$, which are identical or different, are each selected, independently of the other, from hydrogen, hydroxy, alkyl having 1 to 6 carbon atoms inclusive in straight or branched chain, alkoxy having 1 to 6 carbon atoms inclusive in straight or branched chain, halogen selected from fluorine, chlorine, bromine and iodine, nitro, amino, carboxy, alkoxycarbonyl having 1 to 6 carbon atoms inclusive in straight or branched chain, benzyloxycarbonyloxy, phosphonate, sulphonate, $SO_2$—$NH_2$ and $SO_2$—NH-alkyl wherein the term alkyl denotes a saturated hydrocarbon group having 1 to 6 carbon atoms in straight or branched chain, R' is selected from hydrogen, alkyl having 1 to 20 carbon atoms inclusive in straight or branched chain, aralkyl, and cycloalkylalkyl, X is selected from oxygen, sulphur, $CH_2$, and NH, n is selected from the integers 1 and 2, wherein:

"aralkyl" denotes a radical formed by an aryl group selected from phenyl and naphthyl that is bonded to an alkyl radical having 1 to 6 carbon atoms inclusive in straight or branched chain, "cycloalkylalkyl" denotes a radical formed by a cycloalkyl group having 3 to 8 carbon atoms inclusive that is bonded to an alkyl radical having 1 to 6 carbon atoms inclusive in straight or branched chain, a stereoisomeric form thereof, or a pharmaceutically-acceptable addition salt thereof.

2. A compound according to claim 1 wherein n=1 and X represents $CH_2$, a stereoisomeric form thereof, or a pharmaceutically-acceptable addition salt thereof.

3. A compound according to claim 1 wherein:

the carbon atom carrying the radical

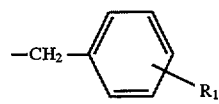

has the S configuration, and the carbon atom carrying the radical

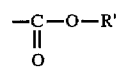

has the S configuration, and
the radicals

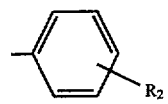

on the one side and

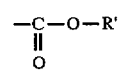

on the other side are cis to one another on the ring containing X a stereoisomeric form thereof, or a pharmaceutically-acceptable addition salt thereof.

4. A compound according to claim 1 which is N-[N-(5R)-[(2S)-2-mercapto-3-(para-hydroxyphenyl)propanoyl] glycyl]-5-(meta-hydroxyphenyl)-L-proline.

5. A compound according to claim 1 which is N-[N-(5R)-[(2S)-(2-mercapto-3-phenylpropanoyl)glycyl]-5-phenyl-L-proline.

6. A compound according to claim 1 which is N-[N-(5R)-[(2S)-(2-mercapto-3-phenylpropanoyl)yl)glycyl]-5-(ortho-hydroxyphenyl)]-L-proline.

7. A compound according to claim 1 which is N-[N-(5R)-[(2S)-[2-mercapto-3-(para-chlorophenyl)propanoyl]glycyl]-5-(ortho-hydroxyphenyl) ]-L-proline.

8. A compound according to claim 1 which is N-[N-(5R)-[(2S)-[2-mercapto-3-(para-aminophenyl)propanoyl]glycyl]-5-phenyl]-L-proline.

9. A mixture comprising two or more stereoisomers of a compound according to claim 1.

10. A mixture comprising two or more stereoisomers of a compound according to claim 2.

11. A mixture comprising two or more stereoisomers of a compound according to claim 3.

12. A pharmaceutical composition useful for inhibiting NEP and ACE comprising an effective amount of a compound as claimed in claim 1 together with a pharmaceutically-acceptable excipient.

13. A method for treating hypertension comprising administering to a mammal in need thereof an effective amount of a compound of claim 1.

14. A method for alleviating symptoms of hypertension associated with a disorder selected from the group consisting of atherosclerosis, cardiac ischemia, hypertrophy, ventricular fibrosis, pulmonary fibrosis, cardiac insufficiency, renal insufficiency, cor pulmonale, pulmonary angina, and vascular wall thickening, wherein said method comprises administering to a mammal afflicted with said disorder an effective amount of a compound of claim 1.

* * * * *

UNITED STATES PATENT AND TRADEMARK OFFICE
CERTIFICATE OF CORRECTION

PATENT NO. : 5,741,781
DATED : April 21, 1998
INVENTOR(S) : B.P. Rogues; M.C. Fournie-Zaluski, Page 1 of 2

It is certified that error appears in the above-indentified patent and that said Letters Patent is hereby corrected as shown below:

Column 3, line 56: "R' is selected from hydrogen, an......." should start a new paragraph.

Column 5, line 33: "The present" should read -- The preferred --.

Column 10, line 57: "0.32" should read -- 0.32g --.

Column 11, lines 15 and 17: In both instances, "degasses" should read -- degassed --.

Column 11. line 59: "1:1 1.09g" should read -- 1:1. 1.09g --.

Column 14, line 25: "Yield: 60%" should read -- Yield: 69% --.

UNITED STATES PATENT AND TRADEMARK OFFICE
CERTIFICATE OF CORRECTION

PATENT NO. : 5,741,781
DATED : April 21, 1998
INVENTOR(S) : B.P. Rogues; M.C. Fournie-Zaluski, It is certified that error appears in the above-indentified patent and that said Letters Patent is hereby corrected as shown below:

Column 16, line 36: Insert -- ( -- before "para-" at the end of the line.

Column 16, line 37: "5(meta-hydroxyphenyl]-" should read -- 5-(meta-hydroxyphenyl)- --.

Signed and Sealed this

Thirtieth Day of June, 1998

Attest:

BRUCE LEHMAN

*Attesting Officer*  *Commissioner of Patents and Trademarks*